US 8,329,761 B2

Dec. 11, 2012

(54) OIL-IN-OIL EMULSIONS

(75) Inventors: Mridula Nair, Penfield, NY (US); Tamara K. Jones, Rochester, NY (US); Mary C. Brick, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 285 days.

This patent is subject to a terminal disclaimer.

(21) Appl. No.: 11/352,586

(22) Filed: Feb. 13, 2006

(65) Prior Publication Data

US 2007/0189998 A1 Aug. 16, 2007

(51) Int. Cl.
*B01F 3/08* (2006.01)
*A61K 9/00* (2006.01)
*A61K 31/66* (2006.01)
*A61K 8/18* (2006.01)

(52) U.S. Cl. .......... 516/20; 516/923; 514/937; 514/136; 424/63; 424/400

(58) Field of Classification Search .................. 424/400, 424/63; 514/937, 136; 516/20; 106/31.25; 922/923
See application file for complete search history.

(56) References Cited

U.S. PATENT DOCUMENTS

| | | | | |
|---|---|---|---|---|
| 1,852,231 A * | 4/1932 | Bryner | | 424/74 |
| 5,043,376 A * | 8/1991 | Sharma et al. | | 524/376 |
| 5,075,026 A * | 12/1991 | Loth et al. | | 510/101 |
| 5,252,555 A * | 10/1993 | Dartnell et al. | | 512/4 |
| 5,705,562 A * | 1/1998 | Hill | | 524/731 |
| 5,889,108 A * | 3/1999 | Zhang | | 524/862 |
| 5,981,474 A * | 11/1999 | Manning et al. | | 514/2 |
| 6,080,394 A | 6/2000 | Lin et al. | | |
| 6,113,931 A * | 9/2000 | Bonda et al. | | 424/401 |
| 6,177,071 B1 * | 1/2001 | Lin et al. | | 424/78.03 |
| 6,238,657 B1 | 5/2001 | Lin et al. | | |
| 6,489,274 B1 * | 12/2002 | LeGrow et al. | | 510/122 |
| 6,645,712 B1 * | 11/2003 | Olijve et al. | | 430/543 |
| 6,688,738 B2 * | 2/2004 | Sarma et al. | | 347/100 |
| 7,205,406 B2 * | 4/2007 | Kataoka et al. | | 544/405 |
| 2002/0155080 A1 * | 10/2002 | Glenn et al. | | 424/70.5 |
| 2003/0228339 A1 * | 12/2003 | El-Nokaly et al. | | 424/401 |
| 2003/0229193 A1 * | 12/2003 | Stepp et al. | | 528/10 |
| 2004/0002429 A1 | 1/2004 | Forbus, Jr. | | |
| 2004/0234475 A1 * | 11/2004 | Lannibois-Drean et al. | | 424/70.12 |
| 2005/0260272 A1 | 11/2005 | Figueiredo et al. | | |

FOREIGN PATENT DOCUMENTS

| | | |
|---|---|---|
| EP | 1 389 468 A1 | 2/2004 |
| WO | WO 03/000396 | 1/2003 |

OTHER PUBLICATIONS

Jachowicz et al., Cosmetics & Tolietries, 1993, 108, pp. 65-72.*
The Journal of Colloid and Interface Science, vol. 195, pp. 101-113, (1997), Article No. CS975158, "Characteristics of Electrorheological Responses in an Emulsion System" by Xiao-Dong Pan and Gareth H. McKinley.
Journal of Drug Deliver Science and Technology, vol. 14 (2), pp. 113-117, (2004), "Formulation of Oil in Oil Emulsions: Potential Drug Reservoirs for Slow Release" by V. Jaitely, T. Sakthivel, G. Magee, A.T. Florence.

* cited by examiner

*Primary Examiner* — Abigail Fisher
(74) *Attorney, Agent, or Firm* — J. Lanny Tucker

(57) ABSTRACT

An stable oil-in-oil emulsion is disclosed containing a first oil phase dispersed as droplets in a continuous second oil phase, which droplets have a number median diameter of 10 nm to 1000 nm, wherein the first oil phase is substantially immiscible in the second oil phase and wherein the first oil phase comprises a liquid organic phosphate compound. In one preferred embodiment, the first oil phase comprises colorants, polymers, and/or other additives, depending on the particular use of the emulsion.

23 Claims, No Drawings

OIL-IN-OIL EMULSIONS

CROSS-REFERENCE TO RELATED APPLICATIONS

The present application is related to U.S. application Ser. No. 11/353,210, filed Feb. 13, 2006 by Jones et al., and entitled, "OIL-IN-OIL DISPERSIONS STABILIZED BY SOLID PARTICLES AND METHODS OF MAKING THE SAME" and to U.S. application Ser. No. 11/352,587, filed Feb. 13, 2006 by Nair et al., and entitled "ELECTRO-OPTICAL MODULATING DISPLAY DEVICES."

FIELD OF THE INVENTION

The invention generally relates to oil-in-oil compositions, for various uses, and in particular, to non-polar oils dispersed in non-polar oils which are capable of effectively solubilizing a variety of materials in the dispersed phase.

BACKGROUND OF THE INVENTION

Colloidal dispersions such as emulsions are dispersed systems consisting of two or more mutually insoluble or sparingly soluble liquids. One of the liquids is usually present in excess and is termed the continuous or external phase, while the liquid dispersed in it is termed the dispersed, discontinuous or internal phase. If the continuous phase consists of water, and the dispersed phase consists of an organic liquid, such as mineral oil, the term oil-in-water (O/W) emulsion is used. If water is finely dispersed in an organic or non-aqueous liquid, a water-in-oil (W/O) emulsion is produced. If two organic liquids are emulsified in each other, the term oil-in-oil (O/O) emulsion or dispersion is used.

While O/W and W/O emulsions containing a non-polar oil such as silicone are common, O/O emulsions in which both phases are essentially non-polar are relatively rare. The Journal of Colloid and Interface Science, Volume 195, Pages 101-113, Article No. CS975158, Jan. 1, 1997, describes certain paraffin oil-in-silicone oil O/O emulsions, as well as certain silicone oil-in-paraffin oil O/O emulsions. Similarly, emulsions of castor oil in silicone oil, as formulations for drug delivery, is described in the Journal of Drug Deliver Science and Technology (2004), 14(2), 113-117.

US Patent Publication No. 2004/0002429 describes lubricant compositions comprising an emulsion comprising a low viscosity, relatively non-polar, hydrocarbon carrier fluid and a minor amount of an immiscible or semi-miscible polar, hydrocarbon fluid.

PCT Appl. WO2003/000396 A1 describes emulsions comprising silicones, as either the continuous phase or the dispersed phase, stabilized by graft and block copolymers, useful for cosmetic applications.

U.S. Pat. No. 6,080,394 A discloses a non-aqueous polar solvent-in-oil emulsion composition containing a non-aqueous polar solvent phase dispersed in a silicone oil continuous phase by an emulsifier. U.S. Pat. No. 6,238,657 B1 describes stabilized O/O emulsions where one of the oil phases is silicone oil while the other oil phase is an organic oil such as mineral oil or castor oil, as well as three-phase aqueous emulsions derived from these and the use of such multi emulsions in personal health care applications.

The formation of O/O emulsions in aliphatic hydrocarbons or the like, such as dodecane, having low-dielectric constants is not trivial. In general, in the formation of emulsions, stable dispersion of droplets or particles result when the attractive potential between two droplets is less than repulsive potential. As repulsive potential is directly proportional to the dielectric constant of the dispersion medium, stable dispersions cannot be easily achieved in a medium of very low dielectric constant such as aliphatic hydrocarbons.

Another issue with which to contend, in the case of particles dispersed in low density hydrocarbon solvents such as dodecane, is settling of the dispersed phase with time, as governed by Stokes law that defines settling velocities of particles in a fluid by the following equation:

$$V = [(2gr^2)(d_1 - d_2)]/9\mu$$

where V=velocity of settling, g=acceleration due to gravity, r=radius of particle or dispersed phase, $d_1$=density of dispersed phase, $d_2$=density of medium, and $\mu$=viscosity of the continuous phase. The issue of settling or creaming of particles is especially relevant to electro-optical modulating display devices in which particles are dispersed in a liquid system, such as electrophoretic, electrowetting, or electrochromic display devices. It is important that the particles in such systems remain neutrally buoyant, neither creaming nor settling. Since viscosity and density mismatches of the dispersed phase, typically solid particles, and the continuous phase are usually so large, techniques such as increasing the viscosity of the continuous phase using polymeric additives are employed to overcome this effect. Such solutions, however, can result is potential drawbacks, for example, causing the electrical mobility of the particles to be compromised.

Given the difficulty and rarity of obtaining oil-in-oil emulsions in general, obtaining such an emulsion in which the two phases have certain desirable properties, which may be advantageous for a given application, is especially challenging. For example, using silicone oil as the dispersed phase can limit the additives that can be solubilized or dispersed effectively in them for many particular applications.

Therefore, there is a need for O/O emulsions in which both the continuous phase and the dispersed phase can be designed to have certain desirable properties, or combinations of properties, which cannot be obtained with prior-art O/O emulsions such as those in which silicone oil is one of the phases. Among the properties that may be desired for both or one of the emulsion phases, depending on the application, include non-polarity as evidenced by a low-dielectric constant. In addition, it may be desired that the dispersed phase is capable of readily incorporating into the dispersed phase, colorants, polymers, or other additives. O/O emulsions having improved or advantageous properties would be useful for a variety of applications involving oil-in-oil emulsions in general. In addition, O/O emulsions with properties not heretofore obtainable, would offer the opportunity for the development of new applications for such materials.

Problem to be Solved by the Invention

It is an object of the present invention to provide colloidally stable O/O emulsions that optionally contain colorants or other additives in dispersed oil droplets and where both the oils used in both the continuous phase and the dispersed phase exhibit relatively low dielectric constants.

SUMMARY OF THE INVENTION

The present invention is directed to overcoming one or more of the problems set forth above. Briefly summarized, according to one aspect of the present invention, a composition comprises an oil-in-oil emulsion containing a first oil phase dispersed as droplets in a second oil phase which is continuous, which droplets have a number median diameter of 10 nanometer (nm) to 1000 nm, wherein the first oil phase is substantially immiscible in the second oil phase and wherein the first oil comprises a liquid organic phosphate compound. In a preferred embodiment, the first oil phase comprises colorants, polymers, and/or other additives.

The O/O emulsions are colloidally stable, do not settle due to extremely low settling rates, remain neutrally buoyant, and preferably have a narrow particle size distribution. In one preferred embodiment, the two phases, the continuous and dispersed phases, have matched refractive indices and the dispersed phase is colored differently than the continuous phase. Such O/O emulsions are advantageous for providing a substantially common dispersed-phase surface for a variety of different colorants due to effective encapsulation of the colorants by the oil in the dispersed oil phase, thereby providing more predictable behavior across a given color series, depending on the application, including imaging systems such as electrically driven displays, liquid toning systems, electrostatic printing inks, and the like.

The term "oil" is defined as a liquid compound that is not miscible with water, generally combustible, although preferably non-volatile, and soluble in ether. The term "oil composition" refers to one or more oils, including a mixture of oils or single oil.

The term "dielectric constant" refers to the measure of the ability of the material to support an electric field and is a measure of the polarity of the material. The dielectric constant "$\epsilon$" of a medium is its ability to reduce the force of attraction F of charged particles $q_1$ and $q_2$ separated at distance r compared to a vacuum. The dielectric constant "$\epsilon$" is defined here by the equation, $F=q_1 q_2/(\epsilon r)$. Dielectric constants for some familiar substances are as follows: water, 80.4; methanol, 33.6; and benzene, 2.3. High-dielectric constant solvents such as water usually have polar functional groups, and often, high dipole moments.

The term "phase" is meant to refer to the entire composition of the phase, including both the liquid oil composition and any additives dissolved or dispersed therein. The terms "oil composition," "fluid carrier," or "fluid" refer to the total organic solvent, or mixture of liquid organic solvents, included in an oil phase, which solvents are inherently liquid in pure form at room temperature, not including inherently solid materials dissolved or dispersed solids in the liquid. Depending on the context, various properties may refer to either the entire composition of a phase or only the oil composition in the phase.

DETAILED DESCRIPTION OF THE INVENTION

The present invention relates to oil-in oil (O/O) emulsions comprising droplets of a discontinuous oil phase containing a low dielectric, essentially non-volatile organic phosphate liquid dispersed in a continuous phase of another low dielectric organic liquid such as an essentially non-volatile hydrocarbon. Preferably, these emulsions further include a colorant, and at least one dispersant for promoting colloidal stability. The emulsions have a number median particle diameter not more than 1000 nm, are colloidally stable and preferably have a narrow particle size distribution. The emulsions can be formulated by a relatively simple, and inexpensive process.

The fluid carrier for the continuous oil phase can be chosen based upon desired properties such as dielectric constant, boiling point, and solubility, depending on the application. In one embodiment a preferred fluid carrier has a low dielectric constant (less than 10), a high boiling point (greater than 100° C. at atmospheric pressure) and a viscosity less than 50 cP at 25° C. The discontinuous phase fluid preferably has a solubility in the continuous phase fluid of less than 1 percent by weight at room temperature. Further, to minimize the settling velocity of the dispersed phase in the O/O emulsion and maintain neutral buoyancy of the emulsion droplets, according to Stokes Law, the difference in density between the discontinuous and continuous phases should be small and the median particle size of the dispersed phase droplets should be sufficiently small.

The choice of oil for the continuous phase may further be based on chemical inertness and chemical compatibility with the dispersed oil phase. The viscosity of the fluid should be low when movement of the dispersed droplets is desired such as in an electro-optically modulated field. For applications in which it is desired to optimize the light transmission through the O/O emulsion, it may be desired to minimize scattering by substantially matching the refractive index of the continuous phase fluid to that of the droplets. As used herein, the refractive index of the continuous phase "is substantially matched" to that of the dispersed phase if the difference between their respective refractive indices is between about zero and about 0.3, preferably between about 0.05 and about 0.2. Additionally, the continuous phase fluid may be chosen to be a poor solvent for some polymers and colorants which are incorporated into the dispersed oil phase, which condition is advantageous in the fabrication of droplets, in order to increase the range of polymeric materials useful in fabricating dispersions of polymers and colorants.

The continuous phase comprises one or more substantially non-polar oils. Organic liquids such as substituted or unsubstituted saturated linear or branched hydrocarbons of the general formula $C_nH_{2n+2}$ where n can be between 6-20, aromatic hydrocarbons, halogenated organic solvents, and silicone oils are a few suitable types of liquid fluids for the continuous phase, which fluid may comprise a single oil or a blend of more than one oil in order to tune its chemical and physical properties. Useful hydrocarbons include, but are not limited to, octane, decane, dodecane, tetradecane, xylene, toluene, naphthalene, hexane, cyclohexane, benzene, the aliphatic hydrocarbons in the ISOPAR series (Exxon), NORPAR (a series of normal paraffinic liquids from Exxon), SHELL-SOL (Shell), and SOL-TROL (Shell), naphtha, STENCIL CLEAN (Qtek) and other petroleum solvents such as superior kerosene, paraffinic liquids, white mineral oil, or suitable mixtures thereof. These materials usually have low densities. Useful examples of silicone oils include, but are not limited to, octamethyl cyclosiloxane and higher molecular weight cyclic siloxanes, poly(methyl phenyl siloxane), hexamethyldisiloxane and polydimethylsiloxane. These materials usually have low densities. Other useful organic liquids include, but are not limited to, organic epoxides, such as, for example, decane epoxide and dodecane epoxide; and vinyl ethers, such as, for example, cyclohexyl vinyl ether.

Furthermore, the continuous oil phase may contain surface modifiers to modify the surface energy or charge of the dispersed oil droplets. Preferably, the continuous phase fluid is clear or transparent and does not itself exhibit any color, although again such is not prohibited by the present invention as discussed above. The continuous phase preferably exhibits a low-dielectric constant and is substantially free of ions.

The dispersed or discontinuous oil phase according to this invention comprises an organic phosphate liquid. Preferred organic phosphate liquids includes, for example, branched or unbranched alkyl, cycloalkyl, alkylcycloalkyl, aryl, and alkylaryl phosphates-based solvents such as dialkyl, diaryl, trialkyl and triaryl phosphates, in which the organic groups may be substituted or unsubstituted, preferred substituents including non-polar groups such as halogens and ethers. In a preferred embodiment, the organic phosphate liquid is a di- or trialkyl phosphate in which each alkyl group of the di- or trialkyl phosphate has one to ten carbon atoms, more preferably two to eight carbon atoms. In another preferred embodiment, the aryl groups may be ring substituted such as, for example, tricresyl phosphate. The alkyl or aryl groups of the di- or trialkyl and aryl phosphate can all be the same or can be different. A particularly preferred trialkyl phosphate is triethyl phosphate. Mixtures of different dialkyl and trialkyl phosphates and diaryl and triaryl phosphates can also be employed. Preferably, these phosphates have a boiling point greater than about 100° C. at atmospheric pressure, a dielectric constant less than 25, and a viscosity less than 100 cP at 25° C. and are substantially insoluble in the continuous phase. Further, after incorporation of polymers and optionally colorants in the dispersed oil phase liquids, the final viscosity of the dispersed oil phase is preferably less than 200 cP and more preferably less than 100 cP at 25° C. for ease of dispersibility in the continuous phase.

The oil fluid for the dispersed phase should be capable of being formed into small droplets in the continuous phase at the temperature at which the emulsion is formed. Processes for forming small droplets include flow-through jets, membranes, nozzles, or orifices, as well as high shear emulsifiers and high pressure homogenizers. The formation of small droplets may be assisted by the use of electrical or sonic fields.

One or more dispersants (including surfactants) can be used to aid in the stabilization and emulsification of droplets in the continuous phase. The dispersant is a compound (including polymers) that is soluble in the continuous phase and sparingly soluble in the dispersed phase and may be added to prevent particle flocculation. Dispersants useful in forming emulsions of the present invention include a variety of ionic and nonionic emulsifiers. In general, dispersants having multiple anchor sites to droplet walls have an advantage in effectively stabilizing the droplets. Blends of dispersants can be used to achieve the necessary requirements for emulsification and stabilization of the droplets and the necessary emulsion properties.

A partial listing representative of preferred dispersants for use in forming the O/O emulsions of this invention includes poly(styrene-co-lauryl methacrylate-co-sulfoethyl methacrylate), poly(vinyltoluene-co-lauryl methacrylate-co-lithium methacrylate), poly(vinyltoluene-co-lauryl methacrylate-co-lithium methacrylate), poly(styrene-co-lauryl methacrylate-co-lithium methacrylate), poly(t-butylstyrene-co-styrene-co-lauryl sulfoethyl methacrylate), poly(t-butylstyrene-co-lauryl methacrylate-co-lithium methacrylate), poly(t-butylstyrene-co-lithium methacrylate), poly(t-butylstyrene-co-lauryl methacrylate-co-lithium methacrylate-co-methacrylic acid), and poly(vinyltoluene-co-lauryl methacrylate-co-methacryloyloxyethyltrimethylammonium p-toluenesulfonate).

Useful block or comb copolymers dispersants include, but are not limited to, AB diblock copolymers of (A) polymers of 2-(N,N-dimethylamino)ethyl methacrylate quaternized with methyl p-toluenesulfonate and (B) poly(2-ethylhexyl methacrylate), and comb graft copolymers with oil soluble tails of poly(12-hydroxystearic acid) and having a molecular weight of about 1800, pendant on an oil-soluble anchor group of poly(methyl methacrylate-methacrylic acid). Useful organic amides include, but are not limited to, polyisobutylene succinimides such as OLOA 11000, OLOA 1200 (Chevron), and N-vinylpyrrolidone polymers, including fatty acid salts of OLOA 11000 such as derived from oleic acid, myristic acid, stearic acid, and arachidic acid. Useful organic zwitterions include, but are not limited to, lecithin. Useful organic phosphates and phosphonates include, but are not limited to, the sodium salts of phosphated mono-and di-glycerides with saturated and unsaturated acid substituents. Examples of suitable polyester amine dispersants include SOLSPERSE 13940 (Noveon) and especially those described in GB-A-2001083, namely comprising the reaction product of a poly (lower alkylene)imine with a polyester having a free carboxylic acid group, in which there are at least two polyester chains attached to each poly(lower alkylene)imine chain. Mixtures of dispersants may be used if desired.

Particularly useful dispersants include compounds comprising at least two different segments, a first segment comprising heteroatoms for absorption to the dispersed phase and a second segment comprising continuous-phase soluble moieties. For example, the first segment may comprises amine groups for attachment and the second segment may comprise, for compatibility with the second phase, repeat units of a monomer. Such compounds are commercially sold under the trademarks OLOA 11000 and SOLSPERSE 13940 (polyesteramine (aziridine-hydroxy stearic acid copolymer), and poly(t-butylstyrene-co-lithium methacrylate). A preferred surfactant is OLOA 11000 a polyethyleneimine substituted succinimide derivative of polyisobutylene.

As indicated above, the dispersed phase of the O/O emulsion preferably can and preferably does include useful ingredients, for example, a pigment, a polymer, a laked pigment, a dye, a pigment-polymer composite, a dye-polymer composite or some combination of the above. Preferably the pigment, polymer, and/or pigment-polymer composite is present in the dispersed first oil phase in a total amount of from 1 to about 50 percent by weight of the dispersed phase, and the oil fluid in the dispersed phase is present in the amount of from 50 to 99 percent by weight of the dispersed phase. In one embodiment, the dispersed oil phase comprises colorant (including pigment or dye) in an amount 1 to 30 percent, preferably 1 to 15 percent, by weight of the dispersed oil phase and 0.1 to 60 percent, preferably 1 to 40 percent, by weight of one or more polymers molecularly dissolved in the dispersed oil phase. A pigment, laked pigment, or pigment-polymer composite, in order to be dispersed in the dispersed oil phase, should have an average particle diameter sufficiently small relative to the diameter of the dispersed oil phase, preferably an average particle diameter on average 10 to 100 nm.

In one embodiment, a pigment-polymer composite may be formed by a physical process such as melt-compounding the polymer and colorant, followed by grinding, attrition, or ball milling. Such composites have been previously used for making conventional xerographic toners and are well known in the art, including the polymers and colorants used to make such toners, and are commercially available from any number of suppliers. A pigment-polymer composite can be mixed into the oil fluid for the dispersed phase by stirring in the composite until the polymer dissolves in the oil. The pigment may also be milled in the oil fluid for the dispersed phase with or without the polymer present. The pigment in the pigment-polymer composite may be present, for example, in an amount of from 0.1 to 80 percent by weight of the pigment-polymer composite. The pigment-polymer composite can be used in amounts of from 1 to about 50 percent by weight of the dispersed phase preferably from 5-30 percent by weight and most preferably from 10-25 percent by weight.

Polymers useful in the practice of this invention for incorporation in the oil droplets with or without a colorant preferably are oil-soluble resins and include, but are not limited to, homopolymers and copolymers such as polyesters, styrenes, e.g. styrene and chlorostyrene; monoolefins, e.g. ethylene, propylene, butylene and isoprene; vinyl esters, e.g. vinyl acetate, vinyl propionate, vinyl benzoate and vinyl butyrate; α-methylene aliphatic monocarboxylic acid esters, e.g. methyl acrylate, ethyl acrylate, butyl acrylate, dodecyl acrylate, octyl acrylate, phenyl acrylate, methyl methacrylate, ethyl methacrylate, butyl methacrylate and dodecyl methacrylate; vinyl ethers, e.g. vinyl methyl ether, vinyl ethyl ether and vinyl butyl ether; and vinyl ketones, e.g. vinyl methyl ketone, vinyl hexyl ketone and vinyl isopropenyl ketone and mixtures thereof. Particularly desirable binder resins include polystyrene resin, polyester resin, styrene/alkyl acrylate copolymers, styrene/alkyl methacrylate copolymers, styrene/acrylonitrile copolymer, styrene/butadiene copolymer, styrene/maleic anhydride copolymer, polyacrylonitrile resin, polyethylene resin and polypropylene resin and mixtures thereof. They further include polyurethane resin, epoxy resin, silicone resin, polyamide resin, polycaprolactone resin, modified rosin, paraffins and waxes and mixtures thereof. In a preferred embodiment, the resins most preferred for the O/O emulsions are polyesters and are soluble in the oil composition of the dispersed oil phase. Suitable polyester resins include polyesters derived from bisphenol A. One preferred polymer is a polyester, for example, TUFTONE NE-303 (Kao Corporation), a polyester copolymer derived from bis-phenol A.

Optional polymers in the dispersed phase may be selected based on the desired properties to be imparted by the inclusion of the polymers, depending on the particular application. For example, a polymer may be used that is functionalized with a charged group in order to control mobility of the dispersed phase through the continuous phase when the emulsion is subjected to an electric or magnetic field. The optional polymers may be selected for other desired properties, for example, to affect the viscosity of the dispersed-phase/droplet.

Dyes useful in this invention can be a pure compound or blends of dyes to achieve a particular color, including black. The dyes can be fluorescent. The dyes can be photoactive, changing to another color or becoming colorless upon irradiation with either visible or ultraviolet light. Dyes could also be polymerizable by, for example, thermal, photochemical or chemical diffusion processes, forming a solid absorbing polymer inside the droplet. Properties desired for the dyes include light fastness, solubility in the suspending liquid, and color. Low cost is also a favorable factor. These dyes are generally chosen from the classes of azo, anthraquinone, and triphenylmethane type dyes and may be chemically modified so as to increase their solubility in the oil phase. Useful azo dyes include, but are not limited to: the Oil Red dyes, and the Sudan Red and Sudan Black series of dyes. Useful anthraquinone dyes include, but are not limited to: the Oil Blue dyes, and the MACROLEX blue series of dyes. Useful triphenylmethane dyes include, but are not limited to, Michler's hydrol, Malachite Green, Crystal Violet, and Auramine O.

A neat pigment can be any pigment, and usually for a light colored particle, pigments such as rutile (titania), anatase (titania), barium sulfate, kaolin, or zinc oxide are useful. Some typical particles have high refractive indices, high scattering coefficients, and low absorption coefficients. Other particles are absorptive, such as carbon black or colored pigments used in paints and inks. The pigment should also be insoluble in the continuous phase. Yellow pigments such as diarylide yellow, HANSA yellow (Clariant), and benzidine yellow have also found use in similar displays. Any other reflective material can be employed for a light colored particle, including non-pigment materials, such as metallic particles.

Useful neat pigments include, but are not limited to, $PbCrO_4$, SUNFAST Blue 15:3, SUNFAST Magenta 122, Cyan blue GT 55-3295 (American Cyanamid Company, Wayne, N.J.), CIBACRON Black BG (Ciba Company, Inc., Newport, Del.), CIBACRON Turquoise Blue G (Ciba), CIBALON Black BGL (Ciba), ORASOL Black BRG (Ciba), ORASOL Black RBL (Ciba), Acetamine Black, CBS (E.I. DuPont de Nemours and Company, Inc., Wilmington, Del., hereinafter abbreviated "DuPont"), CROCEIN scarlet N EX (DuPont) (27290), FIBER BLACK VF (DuPont) (30235), LUXOL FAST BLACK L (DuPont) (Solv. Black 17), NIROSINE Base No. 424 (DuPont) (50415 B), Oil Black BG (DuPont) (Solv. Black 16), ROTALIN Black RM (DuPont), SEVRON Brilliant Red 3B (DuPont); Basic Black DSC (Dye Specialties, Inc.), HECTOLENE BLACK (Dye Specialties, Inc.), AZOSOL Brilliant Blue B (GAF, Dyestuff and Chemical Division, Wayne, N.J.) (Solv. Blue 9), AZOSOL Brilliant Green BA (GAF) (Solv. Green 2), AZOSOL Fast Brilliant Red B (GAF), AZOSOL Fast Orange RA Conc. (GAF) (Solv. Orange 20), AZOSOL Fast Yellow GRA Conc. (GAF) (13900 A), Basic Black KMPA (GAF), BENZOFIX Black CW-CF (GAF) (35435), CELLITAZOL BNFV Ex Soluble CF (GAF) (Disp. Black 9), CELLITON Fast Blue AF Ex Conc (GAF) (Disp. Blue 9), Cyper Black IA (GAF) (Basic Black 3), Diamine Black CAP Ex Conc (GAF) (30235), Diamond Black EAN Hi Con. CF (GAF) (15710), Diamond Black PBBA Ex (GAF) (16505); Direct Deep Black EA Ex CF (GAF) (30235), HANSA Yellow G (GAF) (11680); INDANTHRENE Black BBK Powd. (GAF) (59850), INDOCARBON CLGS Conc. CF (GAF) (53295), KATIGEN Deep Black NND Hi Conc. CF (GAF) (15711), RAPIDOGEN Black 3G (GAF) (Azoic Black 4); SULPHONE Cyanine Black BA-CF (GAF) (26370), ZAMBEZI Black VD Ex Conc. (GAF) (30015); RUBANOX Red CP-1495 (The Sherwin-Williams Company, Cleveland, Ohio) (15630); REGAL 1330 (Cabot Corporation), RAVEN 11® (Columbian Carbon Company, Atlanta, Ga.), (carbon black aggregates with a particle size of about 25 µm), STATEX B-12 (Columbian Carbon Co.) (a furnace black of 33 µm average particle size), and chrome green.

Laked pigments are particles that have a dye precipitated on them and are metal salts of readily soluble anionic dyes. These are dyes of azo, triphenylmethane or anthraquinone structure containing one or more sulphonic or carboxylic acid groupings. They are usually precipitated by a calcium, barium or aluminum salt onto a substrate. Typical examples are Peacock Blue lake (Cl Pigment Blue 24) and Persian orange (lake of Cl Acid Orange 7), and Black M TONER, a mixture of carbon black and black dye precipitated carbon black (GAF).

The pigment-polymer composite may also contain, in addition to pigment and polymer, other additives such as organo-cations, including quaternary ammonium and phosphonium compounds. Examples of these include lauramidopropyltrimethylammonium methylsulfate, octadecyldimethylbenzylammonium m-nitrobenzenesulfonate, methyltriphenylphosphonium tetrafluoroborate, and methyltriphenylphosphonium tosylate.

The process for making the O/O emulsion is carried out, for example, by combining a pigment-polymer composite dispersed in the oil for the discontinuous phase with the oil for the continuous phase, such that the discontinuous phase is present at a weight percent of 1-50 weight percent, preferably 5-40 weight percent of the continuous phase and mixing the ingredients using shear force, for example a homogenizer at room temperature until an O/O emulsion is formed. Any type of mixing and shearing equipment may be used to perform these steps such as a batch mixer, planetary mixer, single or multiple screw extruder, dynamic or static mixer, colloid mill, high pressure homogenizer, sonicator, or a combination thereof. While any high shear type agitation device is applicable to the process of this invention, a preferred homogenizing device is the MICROFLUIDIZER such as Model No. 110T produced by Microfluidics Manufacturing. In this device, the droplets of the first oil phase (discontinuous phase) are dispersed and reduced in size in the second oil phase (continuous phase) in a high shear agitation zone and, upon exiting this zone, the particle size of the dispersed oil is reduced to uniform sized dispersed droplets in the continuous phase. The temperature of the process can be modified to achieve the optimum viscosity for emulsification of the droplets. The number median particle size of the O/O emulsion droplets is not more than 1000 nm and preferably less than 500 nm but at least 10 nm, more preferably at least 25 nm.

The O/O emulsions according to the present invention can be used in a variety of applications, either known or newly developed applications, including electro-optical modulating display devices such as electrophoretic or electrowetting displays. Imaging applications include, for example, migration imaging and liquid toning systems, imaging applications that use electrostatics for ink fractionation and transfer. Industrial applications include, for example, coatings and lubricating films for mechanical devices.

In one particular embodiment of the invention, an O/O emulsion according to the present invention is useful as the display fluid of electro-optical modulated display devices, meaning display devices in which the optical state of an imaging material is modulated or changed by subjecting the imaging material to at least an electric field or the transport of electrons, for example, electrophoretic, electrowetting, and electrochromic display devices. The liquid system preferably contains from about 50 to about 95% by weight of the continuous phase and about 5 to about 50% by weight of colored dispersed oil droplets.

The following examples illustrate the practice of this invention. They are not intended to be exhaustive of all possible variations of the invention.

EXAMPLES

TUFTONE NE-303, a bisphenol A polyester resin polymer (density 1.16 g/cc), used in the examples below was obtained from Kao Specialties Americas LLC a part of Kao Corporation, Japan. The carbon black pigment REGAL 330 (density 1.8 g/cc) used in the examples was obtained from Cabot Corporation, Billerica, Mass. SUNFAST BLUE 15:3 (PB 15:3), and SUNFAST MAGENTA 122 (PR122), the colored pigments were obtained from Sun Chemicals. Triethyl phosphate (TEP), tri-m-cresyl phosphate (TmCP), and n-dodecane were purchased from Aldrich Chemical Co., Milwaukee, Wis. OLOA 11,000 a polyisobutylene succinimide, 62% active in mineral oil was obtained from Chevron in San Ramon, Calif. SOLSPERSE 13940 was obtained from Noveon, and poly(t-butylstyrene-co-lithium methacrylate) containing 3 weight % lithium methacrylate (tBSLM) was made according to the method described in U.S. Pat. No. 3,788,995. The quaternary ammonium and phosphonium additives used were lauramidopropyltrimethylammonium methylsulfate (A), octadecyldimethylbenzylammonium m-nitrobenzenesulfonate (B), methyltriphenylphosphonium tetrafluoroborate (C), and methyltriphenylphosphonium tosylate (D). These were made as described in U.S. Pat. Nos. 4,834,920A and 4,837,391A.

Table 1 below lists various oil phase compositions and their properties. Viscosities were measured using a Brookfield cone/plate viscometer at 25° C. The other parameters were obtained from various published literature sources and the densities of the oil phases containing additives were calculated from weighted averages.

TABLE 1

| Oil Composition | Viscosity (mPa, 25° C.) | Density (g/cc) | Refractive Index | Dielectric Constant (20° C.) | Boiling Point ° C. (atm P) |
|---|---|---|---|---|---|
| TEP | 1.8 | 1.072 | 1.405 | 13.2 | 215 |
| TEP + TUFTONE NE-303 (80/20w/w) | 37.3 | 1.09 | | | |
| TEP + TUFTONE NE-303 + REGAL 330 (80/15/5w/w/w) | 29.4 | 1.12 | | | |
| Dodecane | 1.38 | 0.75 | 1.421 | 2.01 | 215 |
| Dodecane + OLOA 11000 (5 wt %) | 1.8 | | | | |
| TmCP | 57 | 1.15 | 1.557 | 6.7 | 275 |

Example 1

A pigment-polymer resin composite (4 g) comprising 25 weight % Regal 330 and 75 weight % TUFTONE NE-303 polymer was dissolved in 16 grams of TEP at ambient temperature. This was dispersed in 76 g of dodecane containing 4 g of OLOA 11000 (100% active), such that the ratio of the dispersed phase to the dispersant is 5:1, using an overhead SILVERSON L4R mixer from Silverson for one minute at maximum speed. The resultant dispersion was homogenized using a MICROFLUIDIZER Model #110T from Microfluidics at a pressure of 12,000 lbs/sq inch until a fine dispersion was obtained. The number median D(n), particle size was measured using a MALVERN ZETASIZER ZS that uses low angle laser light scattering method and a 633 nm wavelength, 4 mW He—Ne laser. D(n) is the particle size which divides the population exactly into two equal halves such that there is 50% distribution above this value and 50% below and is listed in Table 2 below. The emulsion described in this example and the following examples were stable for several months at ambient temperature as shown by minimum settling and unchanged particle size. The average settling velocity of the O/O emulsions shown in all the examples below as calculated by Stokes Law is approximately $1 \times 10^{-8}$ ms$^{-1}$.

Examples 2-3

The same method as in the above Example 1 was used to make all the O/O dispersions described in these examples below, except in these examples, REGAL 330 was substituted with the colored pigments PR122 and PB 15:3.

Example 4-5

Example 4 was prepared as in Example 1 except that the oil for the dispersed phase was replaced with TmCP. Example 5 was made the same as Example 1 but without the colorant.

TABLE 2

| Example | Pigment | Oil in Dispersed Phase | D(n)nm | CV |
|---|---|---|---|---|
| 1 | REGAL 330 | TEP | 266 | 32 |
| 2 | PR122 | TEP | 143 | 26 |
| 3 | PB 15:3 | TEP | 233 | 26 |
| 4 | REGAL 330 | TmCP | 169 | 37 |
| 5 | None | TEP | 174 | 35 |

Table 2 above shows the O/O emulsions made with different colorants in the dispersed phase oils. All the particles were small as seen by the number median size (Dn) and had similar coefficients of variance value (CV). The emulsion was stable for several months at ambient temperature as described in Example 1.

Examples 6-8

The O/O emulsions for these examples were made as in Example 1 except that the pigment-polymer composite had ammonium or phosphonium additives as shown in Table 3. These additives were used to replace 5 weight % of the TUFTONE polymer. Table 3 below shows the median particle sizes were small and the CV consistent and narrow.

TABLE 3

| Example | Quaternary additive in pigment polymer composite | D(n)nm | CV |
|---|---|---|---|
| 6 | B | 154 | 49 |
| 7 | C | 146 | 44 |
| 8 | D | 137 | 44 |

The emulsions were stable for several months at ambient temperature as described in Example 1.

Examples 9-13

In these examples, other dispersants were used to make the O/O emulsions. The pigment-polymer composite was the same as that used in the above Examples 6-8. As Table 4 below shows, Examples 9-12 made using tBSLM as the dispersant and the ratios as specified in Examples 6-8, gave a small median particle size and a tight CV. Examples 13 was again made the same way except SOLSPERSE 13940 was used instead of tBSLM. A smaller particle size of the emulsion was obtained.

TABLE 4

| Example | Quaternary additive in pigment-polymer composite | Dispersant (Ratio of Dispersed Phase to Dispersant) | D(n)nm | CV |
|---|---|---|---|---|
| 9 | D | TBSLM | 214 | 32 |
| 10 | C | TBSLM | 187 | 30 |
| 11 | A | TBSLM | 216 | 31 |
| 12 | B | TBSLM | 245 | 28 |
| 13 | A | SOLSPERSE 13940 (5:1) | 156 | 41 |

The emulsions described in these examples were stable for several months at ambient temperature as described in Example 1.

Examples 14-17

In these examples, the pigment-polymer composite was the same as that used in Example 1 except that fatty acid salts of OLOA 11000 derived from oleic acid, myristic acid, stearic acid, and arachidic acid were used as dispersants to make the O/O emulsions. As Table 5 below shows, Examples 14-17 made using the quaternary fatty acid salts as dispersants gave consistently small median particle sizes and tight CV.

TABLE 5

| Example | Fatty acid used with OLOA 11000 | D(n)nm | CV |
|---|---|---|---|
| 14 | Oleic | 284 | 46 |
| 15 | Myristic | 294 | 63 |
| 16 | Stearic | 262 | 42 |
| 17 | Arachidic | 272 | 46 |

The emulsions described in these examples were stable for several months at ambient temperature as described in Example 1.

The invention has been described with reference to a preferred embodiment. However, it will be appreciated that variations and modifications can be effected by a person of ordinary skill in the art without departing from the scope of the invention.

The invention claimed is:

1. An oil composition comprising a colloidally stable, water free oil-in-oil emulsion containing a first oil phase dispersed as droplets in a continuous non-polar second oil phase, which droplets have a number median diameter of 10 nm to 1000 nm, wherein the first oil phase comprises one or more oils in a first oil composition and the second oil phase comprises one or more oils in a second oil composition, the first oil composition comprises one or more liquid organic phosphate compounds, the first oil phase optionally further comprising colorant and/or polymer, wherein the one or more liquid organic phosphate compounds in the first oil composition is present in the amount of from 50 to 99 percent by weight of the dispersed first oil phase, wherein the continuous second oil phase has a dielectric constant less than 10, and wherein the second oil phase comprises one or more solvents selected from the group consisting of substituted or unsubstituted non-polar hydrocarbons, substituted or unsubstituted $C_6$-$C_{20}$ alkanes, substituted or unsubstituted aromatic hydrocarbons, and mixtures thereof.

2. The composition of claim 1 further comprising a dispersant.

3. The composition of claim 2 wherein the dispersant is an organic polymer that is substantially soluble in the continuous phase but not the dispersed phase.

4. The composition of claim 1 wherein refractive index of the continuous second oil phase is substantially matched to that of the dispersed first oil phase such that the difference between respective refractive indices of the phases is between about zero and about 0.3.

5. The composition of claim 4 wherein the difference between the respective refractive indices is between about 0.05 and about 0.2.

6. The composition of claim 1 wherein dielectric constant of the first and second oil compositions, respectively, in the two phases are both independently less than 25, before the addition of any solid additives to the oil compositions of the phases.

7. The composition of claim 1 wherein the second oil phase comprises a solvent selected from the group consisting of octane, decane, dodecane, tetradecane, xylene, toluene, naphthalene, hexane, cyclohexane, benzene, petroleum solvents, paraffinic liquids, white mineral oil, and mixtures thereof.

8. The composition of claim 1 wherein the liquid organic phosphate compound has a boiling point of about 100° C. or greater at atmospheric pressure, a dielectric constant less than 25, and a viscosity less than 100 cP at 25° C.

9. The composition of claim 1 where the first oil phase, including the first oil composition and optional polymers, colorants, or other additives, has a viscosity less than 200 cP at 25° C.

10. The composition of claim 1 wherein the one or more oils in the first oil composition is selected from the group consisting of trialkylphosphates, triarylphosphates, and mixtures thereof.

11. The composition of claim 1 wherein the boiling points of the dispersed first oil phase and the continuous second oil phase, respectively, is independently greater than 100° C. at atmospheric pressure.

12. The composition of claim 1 wherein the dispersed first oil phase comprises a molecularly dissolved polymer.

13. The composition of claim 12 wherein the polymer is polyester.

14. The composition of claim 1 wherein the dispersed first oil phase further comprises a colorant.

15. The composition of claim 14 wherein the colorant in the dispersed first oil phase is a dye or pigment-based colorant.

16. The composition of claim 15 wherein the colorant is a pigment having an average particle diameter of 10 to 100 nm.

17. The composition of claim 15 wherein the pigment-based colorant comprises a pigment-polymer composite in which a pigment is dispersed in a polymer.

18. The composition of claim 17 wherein the pigment-polymer composite is a product of melt compounding a colorant and a polymer, solidifying the melt, and then grinding or otherwise physically dividing solid melt into particles.

19. The composition of claim 1 wherein the dispersed first oil phase comprises both a colorant and a molecularly dissolved polymer.

20. The composition of claim 1 wherein the dispersed first oil phase comprises a colorant in an amount from 1 to 30 percent by weight of the dispersed first oil phase.

21. The composition of claim 1 wherein a pigment, a polymer, and/or a pigment-polymer composite is present in the dispersed first oil phase in a total amount of from 1 to 50 percent by weight of the dispersed phase.

22. The composition of claim 1 wherein the dispersed first oil phase is present in the amount of 1 to 50 weight percent of the continuous second oil phase.

23. An oil composition comprising a colloidally stable, water free oil-in-oil emulsion containing a first oil phase dispersed as droplets in a continuous non-polar second oil phase, which droplets have a number median diameter of 10 nm to 1000 nm, wherein the first oil phase comprises one or more oils in a first oil composition and the second oil phase comprises one or more oils in a second oil composition, wherein the one or more oils in the first oil composition comprises one or more liquid organic phosphate compounds selected from the group consisting of branched or unbranched alkyl, cycloalkyl, alkylcycloalkyl, aryl, and alkylaryl phosphates, in which organic groups in the liquid organic phosphate compounds may be substituted or unsubstituted non-polar groups, and mixtures thereof, wherein the first oil phase further comprises both colorant and polymer, wherein a pigment, a polymer, and/or a pigment-polymer composite is present in the dispersed phase and wherein the one or more oils in the first oil composition is present in the amount of from 50 to 99 percent by weight of the dispersed first oil phase wherein the continuous second oil phase has a dielectric constant less than 10 and wherein the second oil phase comprises one or more solvents selected from the group consisting of substituted or unsubstituted non-polar hydrocarbons, substituted or unsubstituted $C_6$-$C_{20}$ alkanes, substituted or unsubstituted aromatic hydrocarbons, and mixtures thereof.

* * * * *